(12) United States Patent
Alexander et al.

(10) Patent No.: US 12,427,342 B2
(45) Date of Patent: Sep. 30, 2025

(54) CHERENKOV IMAGING-BASED SOLUTION FOR MR-LINAC QUALITY ASSURANCE

(71) Applicant: Trustees of Dartmouth College, Hanover, NH (US)

(72) Inventors: Daniel A. Alexander, Hanover, NH (US); Jacqueline Andreozzi, Hanover, NH (US); Petr Bruza, Lebanon, NH (US); Rongxiao Zhang, Lebanon, NH (US); David J. Gladstone, Lebanon, NH (US)

(73) Assignees: TRUSTEES OF DARTMOUTH COLLEGE, Hanover, NH (US); MARY HITCHCOCK MEMORIAL HOSPITAL, FOR ITSELF AND ON BEHALF OF DARTMOUTH-HITCHCOCK CLINIC, Lebanon, NH (US)

( * ) Notice: Subject to any disclaimer, the term of this patent is extended or adjusted under 35 U.S.C. 154(b) by 210 days.

(21) Appl. No.: 18/280,289

(22) PCT Filed: Mar. 7, 2022

(86) PCT No.: PCT/US2022/019164
§ 371 (c)(1),
(2) Date: Sep. 5, 2023

(87) PCT Pub. No.: WO2022/187743
PCT Pub. Date: Sep. 9, 2022

(65) Prior Publication Data
US 2024/0066324 A1    Feb. 29, 2024

Related U.S. Application Data

(60) Provisional application No. 63/157,240, filed on Mar. 5, 2021.

(51) Int. Cl.
*A61N 5/10* (2006.01)

(52) U.S. Cl.
CPC .... *A61N 5/1075* (2013.01); *A61N 2005/1055* (2013.01); *A61N 2005/1076* (2013.01)

(58) Field of Classification Search
CPC ........... A61B 6/58; A61B 6/582; A61B 6/583; A61B 6/584; A61B 6/08;
(Continued)

(56) References Cited

U.S. PATENT DOCUMENTS

| 4,873,708 A | 10/1989 | Cusano et al. |
| 9,782,607 B2 | 10/2017 | Wiersma et al. |

(Continued)

FOREIGN PATENT DOCUMENTS

| JP | 2021112589 A | * | 8/2021 | ............. A61B 6/583 |
| WO | 2020020840 A1 | | 1/2020 | |
| WO | 2021033823 A1 | | 2/2021 | |

OTHER PUBLICATIONS

WIPO, International Search Report for PCT/US2022/019164, Jun. 22, 2022.

(Continued)

*Primary Examiner* — Don K Wong
(74) *Attorney, Agent, or Firm* — Hodgson Russ LLP

(57) ABSTRACT

A system includes a cylindrical phantom and a conical structure disposed in the phantom. The conical structure is shaped as a frustum and emits Cherenkov radiation when exposed to ionizing radiation. The system can be used for calibration of an MR-Linac system by exposing the system to ionizing radiation. The Cherenkov radiation can be imaged during exposure to ionizing radiation.

17 Claims, 7 Drawing Sheets

(58) Field of Classification Search
CPC .......... A61N 2005/1076; A61N 5/1075; A61N 5/1048; A61N 5/1049; G01R 33/58
See application file for complete search history.

(56) References Cited

U.S. PATENT DOCUMENTS

| | | |
|---|---|---|
| 2017/0157427 A1 | 6/2017 | Xing et al. |
| 2020/0022660 A1 | 1/2020 | Sha et al. |
| 2020/0057165 A1 | 2/2020 | Archambault et al. |

OTHER PUBLICATIONS

Mittauer et al., "Characterization and longitudinal assessment of daily quality assurance for an MR-guided radiotherapy (MRgRT) linac," Journal of Applied Clinical Medical Physics, 2019, pp. 27-36, vol. 20, Issue 11.

Latifi et al., "A Method to Determine the Coincidence of MRI-Guided Linac Radiation and Magnetic Isocenters," Technology in Cancer Research & Treatment, 2019, vol. 18, No. I-6.

Dorsch et al., "Measurement of isocenter alignment accuracy and image distortion of an 0.35 T MR-Linac system," Physics in Medicine & Biology, 2019, vol. 64, No. 20.

Miao et al., "Cherenkov imaging for linac beam shape analysis as a remote electronic quality assessment verification tool," Medical Physics, Feb. 2019, pp. 811-821, vol. 48, No. 2.

Ashraf et al., "Optical imaging provides rapid verification of static small beams, radiosurgery, and VMAT plans with millimeter resolution," Medical Physics, Nov. 2019, pp. 5227-5237, vol. 46, No. 11.

Andreozzi et al., "Remote Cherenkov imaging-based quality assurance of a magnetic resonance image-guided radiotherapy system," Medical Physics, Jun. 2018, pp. 2647-2659, vol. 46, No. 6.

Alexander et al., "Scintillation Imaging as a High-Resolution, Remote, Versatile 2D Detection System for MR-Linac Quality Assurance," Medical Physics, Sep. 2020, pp. 3861-3869, vol. 47, No. 9.

Gonzalez et al., "A procedure to determine the radiation isocenter size in a linear accelerator," Medical Physics, Jun. 2004, pp. 1489-1493, vol. 31, No. 6.

* cited by examiner

CHERENKOV IMAGING-BASED SOLUTION FOR MR-LINAC QUALITY ASSURANCE

CROSS-REFERENCE TO RELATED APPLICATIONS

This application claims priority to the provisional patent application filed Mar. 5, 2021 and assigned U.S. App. No. 63/157,240, the disclosure of which is hereby incorporated by reference.

STATEMENT REGARDING FEDERALLY-SPONSORED RESEARCH OR DEVELOPMENT

This invention was made with government support under grants R01 EB023909 and R44 CA232879 awarded by the National Institutes of Health. The government has certain rights in the invention.

FIELD OF THE DISCLOSURE

This disclosure relates to quality assurance for imaging systems.

BACKGROUND OF THE DISCLOSURE

The installation of magnetic resonance guided radiation therapy systems (MRgRT) has introduced the benefits of real-time magnetic resonance (MR) imaging to adaptive radiation therapy planning on a magnetic resonance guided linear accelerator (referred to as MR-Linac or MRI-Linac) platform. These benefits include superior soft tissue contrast compared to x-ray imaging and continuous imaging during treatment, enabling high positional accuracy and robust inter-fraction adjustments. However, this technology has more quality assurance (QA) procedure complications than with conventional accelerators. This includes the compatibility of traditional detectors with the magnetic environment and the effect of the magnetic field on dosimetric measurements. Daily QA of a traditional linac can be performed with an onboard imager or detector array capable of measuring both the therapeutic MV beam and the kV imaging beam to assess output and isocenter verification. This convenience does not carry over to MR-Linac systems, as the MR modality is not readily probed by these detectors and onboard x-ray imaging device are not universally available on MR-Linac models.

One particular daily QA measurement that is a challenge on MR-Linac systems is the verification of the mechanical, imaging, and radiation isocenter coincidence, described in the AAPM Task Group 142 report with an acceptable tolerance of ≤2 mm. This parameter can be used to verify against baseline, and there is responsibility placed on the physicist to determine an adequate method to evaluate the consistency of the alignment. There have been procedures in the literature describing methods to perform this measurement, based on film, polymer gel, spatial localization of individual ion chambers, or MR-compatible ion chamber arrays. These methods can be cumbersome and time-consuming either with setup or post-exposure processing. These methods also can rely on reduced information to infer 3D isocenter coincidence. Currently, for the MRIdian system (ViewRay, Cleveland, OH, USA), the vendor-recommended method involves two pieces of radiochromic film. The first is embedded in the provided cylindrical daily QA phantom and the second is wrapped around the outer diameter, and subsequently irradiating with a five-field star shot. The readout of these films is then performed in post processing, which yields the radiation isocenter in the x-z plane, as well as along the y-axis since the beam is forward-peaked with the lack of flattening filter. However, to relate this measurement to the imaging isocenter, the laser marks must be manually marked on the film and analyzed in the post-processing coordinate system in order to translate back to the treatment coordinate system. While accurate, this process is very time consuming and not suited to be carried out on a daily basis. However, there are limited other options to directly quantify the 3D isocentricity.

Improved systems and methods to perform QA are needed.

BRIEF SUMMARY OF THE DISCLOSURE

A Cherenkov imaging-based quality assurance system includes an enclosed cylindrical plastic phantom containing a conical structure that emits Cherenkov radiation when exposed to therapeutic ionizing radiation and a camera capable of time-gated imaging of Cherenkov light. The system can be used for QA, such as with a daily use. The conical structure is visible by the camera and oriented such that the diameter increases with distance from the camera. The structure contains a hollow conical cavity on the rear side that comes to a point at the physical center of the structure. This center is also marked on front surface of the structure with a crosshair for the lateral and vertical directions, and a ring for the axial direction. Cherenkov emission captured by the camera during irradiation of the phantom acts as a surrogate of radiation dose to the conical structure, and, therefore, the system is capable of measuring the distribution of radiation dose delivered to the structure in the imaging plane. The conical shape of the structure adds additional information about dose distribution along the axis perpendicular to the imaging plane due to the angled surface that is sensitive to changes that dimension. The camera can capture a 2D image, but by imaging a cone where the angle is 45° from the plane of the image, dose can be observed in the plane of the image (x and z) as well as along the axis perpendicular to the image (y) because the cone is 45° from both the image plane and that axis.

By irradiating the phantom with a sheet of radiation parallel to the imaging plane and smaller than the height of the conical structure, the axial position of that beam is encoded as the diameter of the circular intersection of the beam with the structure, where that intersection yields Cherenkov emission. This framework allows for the physical measurement in three dimensions of the isocenter of the radiation system relative to the position of the phantom via the marks (e.g., crosshairs for the x-y plane and etched ring for the y-axis) on the structure surface. This is extended to the reference frame of the imaging system by scanning the phantom using the on-board imaging system and denoting the physical position of the center of the structure in three dimensions on the resulting scan.

Embodiments disclosed herein provide the capability to measure the imaging-radiation isocenter coincidence of a therapeutic linear accelerator in a manner that is simplified and more efficient. It allows for analysis of the result immediately after localized data acquisition, which can avoid post-exposure readout of dosimeters. The phantom may be entirely enclosed, which simplifies daily setup. No adjustments may be needed after initial daily setup to capture all necessary data. The system is also compatible with clinically-available ionization chambers for machine output measurements.

A robust Cherenkov imaging-based solution was demonstrated for MR-Linac periodic (e.g., daily) QA, including mechanical-imaging-radiation isocenter coincidence verification.

A system is provided in a first embodiment. The system includes a cylindrical phantom a conical structure disposed in the phantom. The conical structure is shaped as a frustum and emits Cherenkov radiation when exposed to ionizing radiation.

The conical structure can be fabricated of a radioluminescent material configured to enhance signal-to-noise.

In an instance, the cylindrical phantom is acrylic.

The conical structure can be fully enclosed in the cylindrical phantom.

The conical structure can be held using spacers.

The cylindrical phantom can be sealed such that it is capable of holding a liquid.

An outer housing of the cylindrical phantom can define a hollowed plug configured to hold an ion chamber. The conical structure can further include a crosshair and a ring on a surface opposite the hollowed plug. The crosshair and the ring are used for lateral, vertical, and axial alignment.

The conical structure can define a cavity in the interior of the frustum that comes to a point at a center of the cylindrical phantom.

A method is provided in a second embodiment. The method includes providing a system that includes a cylindrical phantom a conical structure disposed in the phantom. The conical structure is shaped as a frustum and emits Cherenkov radiation when exposed to ionizing radiation. The system is exposed to ionizing radiation. Using a processor, an MR-Linac is calibrated using measurements from the exposing.

The Cherenkov radiation can be imaged during exposure to ionizing radiation.

The cylindrical phantom can be configured to be a surrogate of radiation dose to the conical structure such that distribution of the radiation dose delivered to the system in the imaging plane is determined.

The cylindrical phantom can be irradiated with a sheet of radiation parallel to an imaging plane and that is smaller than a height of the conical structure. This provides a diameter of a circular intersection of the radiation with the conical structure and providing an axial position of the radiation.

The calibration can include measurement in three dimensions of an isocenter of the system relative to a position of the cylindrical phantom using marks on a surface of the conical structure.

The calibration can use a flat field image, a pixel size, and/or a diameter-to-longitudinal position calibration.

A Cherenkov image and/or a star shot image can be used to determine a difference between a center of the cylindrical phantom and a radiation isocenter.

The processor can be in electronic communication with a camera.

In a third embodiment, a computer program product comprises a non-transitory computer readable storage medium having a computer readable program embodied therewith. The computer readable program configured to carry out the calibrating of the second embodiment.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Cherenkov is proportional to dose deposited by monoenergetic x-ray beams, but the energy dependence of Cherenkov emission complicates the relation to dose for realistic clinical x-ray beams. However, Cherenkov emission is a beneficial tool for QA measurements related to beam geometry, as Cherenkov intensity is monotonically related to dose. Cherenkov and scintillation imaging have been demonstrated as useful methods for various QA procedures in both traditional image guided radiotherapy and MRgRT, and this is exploited in this context for high-resolution 3D positional measurement of the radiation beam. The Cherenkov imaging-based solution disclosed herein can measure mechanical-imaging-radiation isocenter coincidence on MR-Linac systems, such as the MRIdian system. The design disclosed herein can be referred to as Visual Isocenter Position Enhanced Review (VIPER). This system includes or consists of a physical phantom and analysis software application. The phantom can be fully enclosed with design considerations for compatibility with the existing daily QA phantom jig and conventional ion chamber output measurement.

Figure 5:
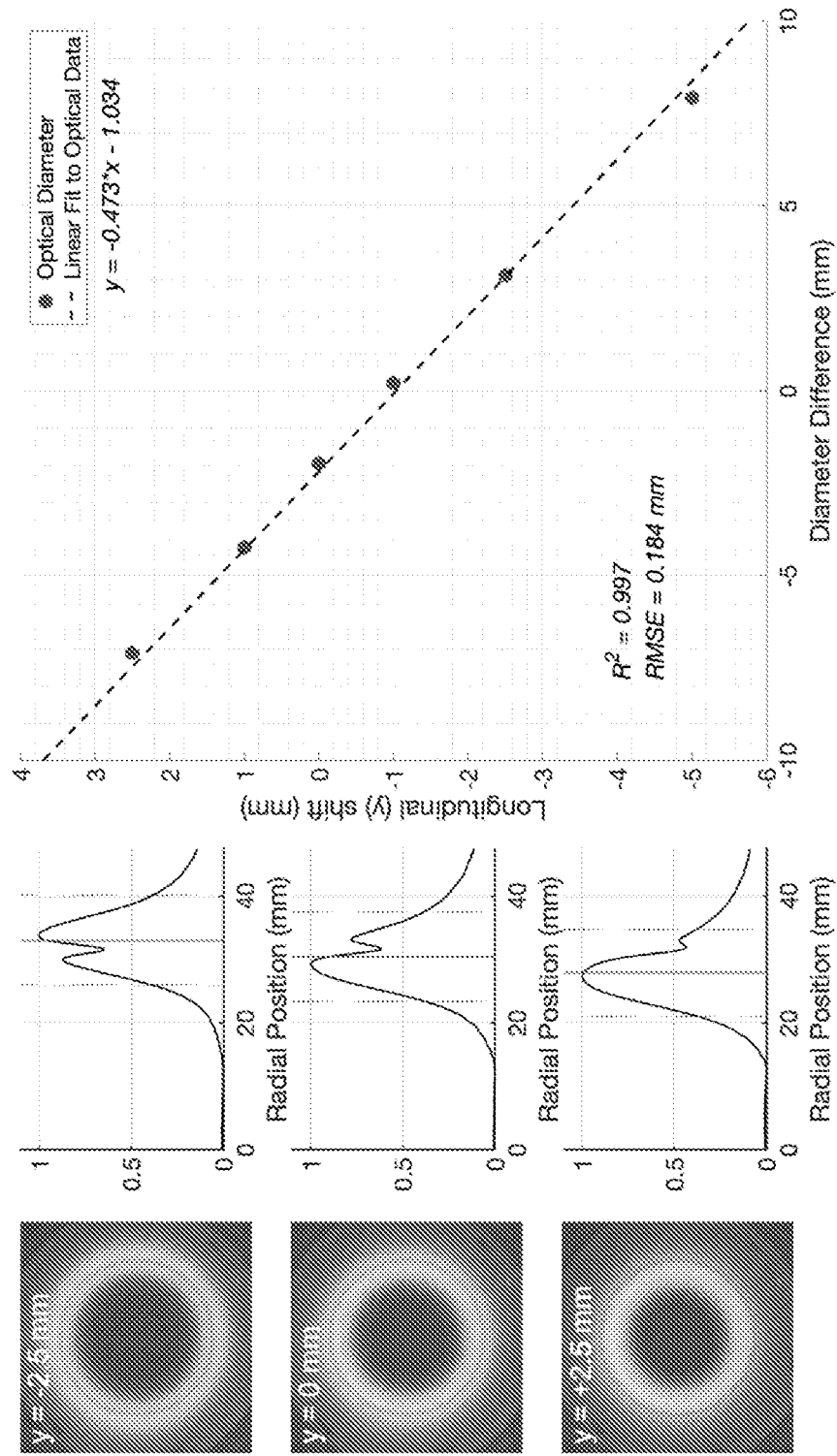
FIG. 5 includes results from the diameter-to-longitudinal position calibration, including select Cherenkov images (left), corresponding normalized average radial profiles (center), and linear fit to the longitudinal shift versus ring diameter difference data (right), wherein positions of the 40% maximum rising and falling edges are shown with a dotted line, while extracted optical radius is shown with a solid vertical line.
Figure 6:
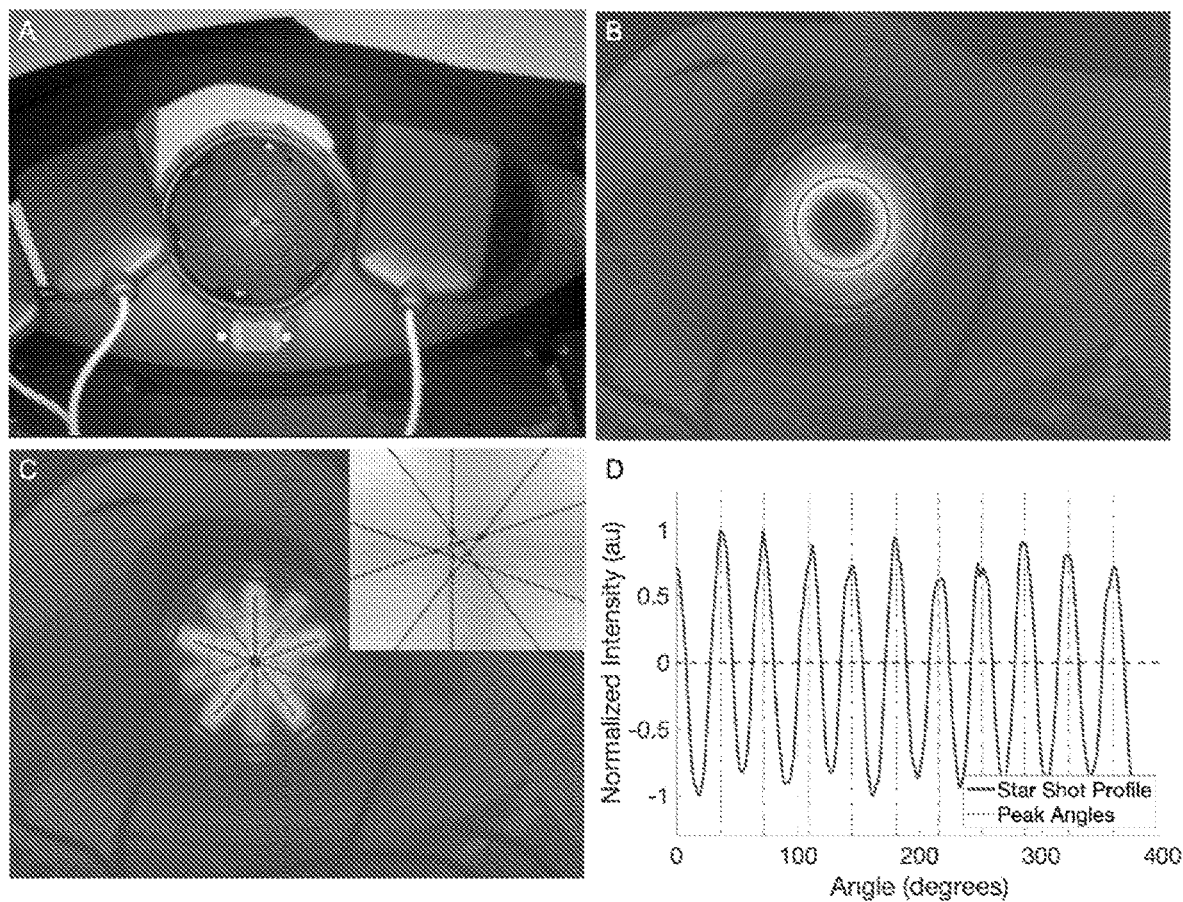
FIG. 6A includes results of the isocenter coincidence analysis from the software with a background image of the phantom with the crosshair center and etched ring highlighted.
FIG. 6B shows the optical ring detected (shown with a circle) overlaid on the Cherenkov image from the sheet irradiation for isocenter detection along the y-axis.
FIG. 6C shows analysis overlaid on the star shot Cherenkov image, along with minimum circle in the zoomed-in subplot for isocenter localization in the x-z plane (minimum radius found to be 0.34 mm)
FIG. 6D shows a circular star shot profile acquired from the analysis in FIG. 6C.
Figure 7:
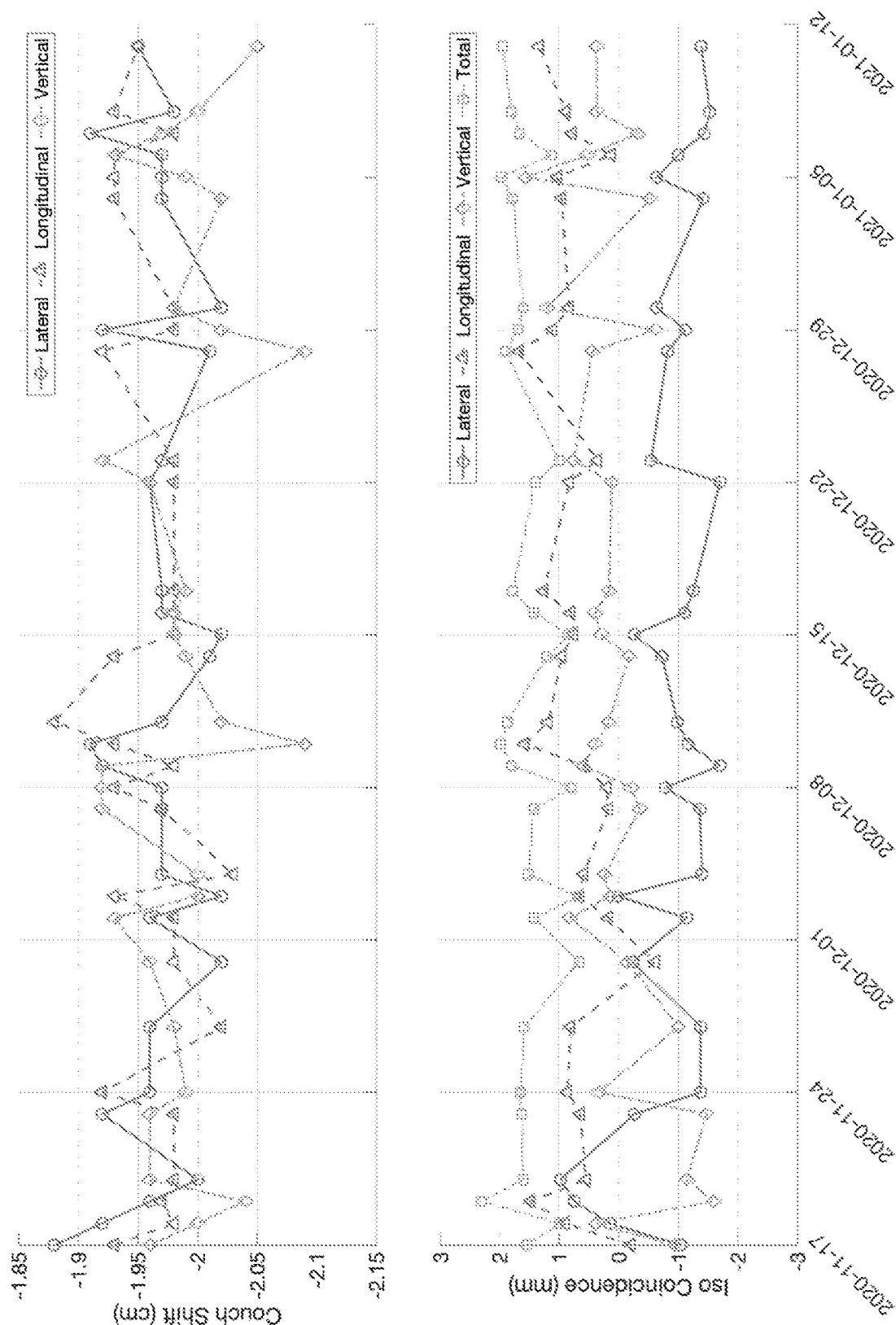
FIG. 7 shows results of an eight-week longitudinal analysis shows couch shifts (top) and 3D isocenter coincidence measurements (bottom), tracked daily.

Embodiments disclosed herein include a phantom and software to perform QA using Cherenkov imaging to determine the relative position of the radiation isocenter. By using an embedded plastic target shown in FIG. 1A-1C that emits Cherenkov radiation and is visible on MRI with high contrast, the positions of the radiation isocenter and MRI imaging isocenter can be related via landmarks on the phantom by delivering radiation in a specified geometry. The positions can be determined as shown in FIG. 4A to FIG. 6D. The conical shape allows for information along the optical axis (y-direction) to be readily imaged in the x-z plane by the camera (FIG. 6A). The phantom was set up daily (FIG. 7) with a 2 cm shift in each direction and shifts to isocenter were calculated and applied by performing an image registration between the new and baseline scans, using the manufacturer-provided tool. Couch shifts in FIG. 7 are compared to −2 cm baseline (dotted line). Mean isocenter coincidence in 3D was found to be 1.5 mm±0.4 mm. Failure rate (3D measurement outside 2 mm tolerance) was 1/31 (3%). High variability is attributed to low relative spatial resolution on the MR images (minimum possible voxel size=1.5 mm).

A fully enclosed acrylic cylindrical phantom was designed to be mountable to the existing jig, indexable to the treatment couch. While acrylic is disclosed, other plastics can be used for the cylindrical phantom. The dimensions of the cylindrical phantom and tabs on the bottom of the front and rear faceplates can enable use of the existing jig. An acrylonitrile butadiene styrene (ABS) plastic conical structure was fixed inside the phantom, held in place with 3D-printed spacers and filled with water allowing for high edge contrast on MR imaging scans. The spacers were fabricated of a 3D printing plastic filament. Both a star shot plan and a four-angle sheet beam plan were delivered to the phantom. The star shot plan allowed for radiation isocenter localization in the x-z plane (A/P and L/R directions) relative to physical landmarks on the phantom. The four-angle sheet beam plan allowed for the longitudinal position of the sheet beam to be encoded as a ring of Cherenkov radiation emitted from the phantom, allowing for isocenter localization on the y-axis (S/I directions). A software application can perform near-real-time analysis of the data by any clinical user.

Calibration procedures show that linearity between longitudinal position and optical ring diameter is high ($R^2 > 0.99$), and that root-mean-square error (RMSE) is low (0.184 mm). The star shot analysis showed a minimum circle radius of 0.34 mm. The final isocenter coincidence measurements were in the lateral, longitudinal, and vertical directions were −0.61 mm, 0.55 mm, and −0.14 mm respectively, and the total 3D distance coincidence was 0.83 mm, with each of these being below the 2 mm tolerance. Thus, embodiments disclosed herein provide an efficient, MR safe, all-in-one method for acquisition and near-real-time analysis of isocenter coincidence data. This provides a direct measurement of the 3D isocentricity.

Embodiments disclosed herein can be used with or in a linear accelerator, radiation therapy system, computed tomography (CT) imaging system, proton therapy system, magnetic resonance imaging (MRI), or other imaging systems.

Figure 1:
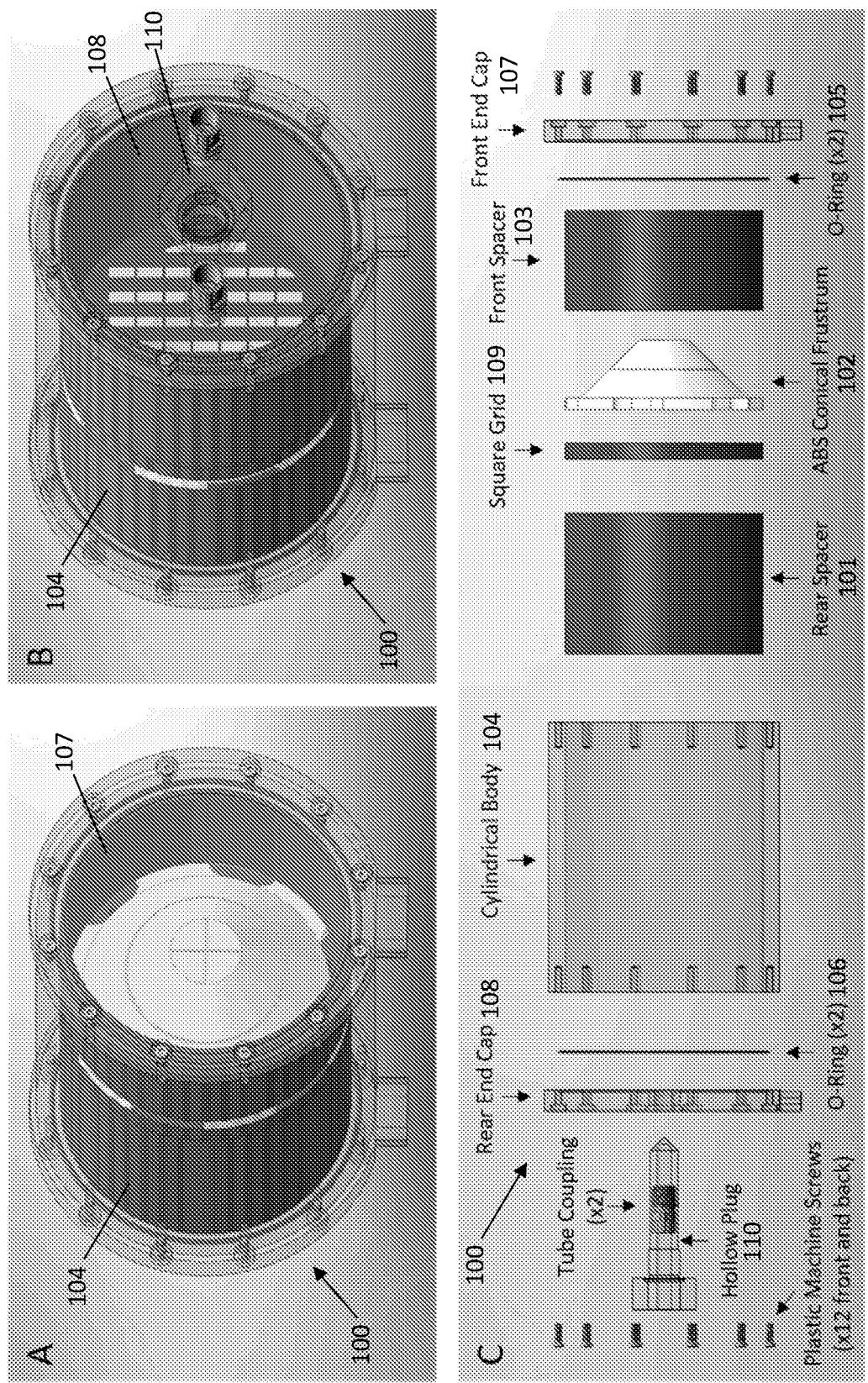
FIG. 1A shows a 3D view from the front of an embodiment of the phantom in accordance with the present disclosure.
FIG. 1B shows the phantom of FIG. 1A from the rear.
FIG. 1C shows an exploded view of the phantom of FIG. 1A.
Figure 2:
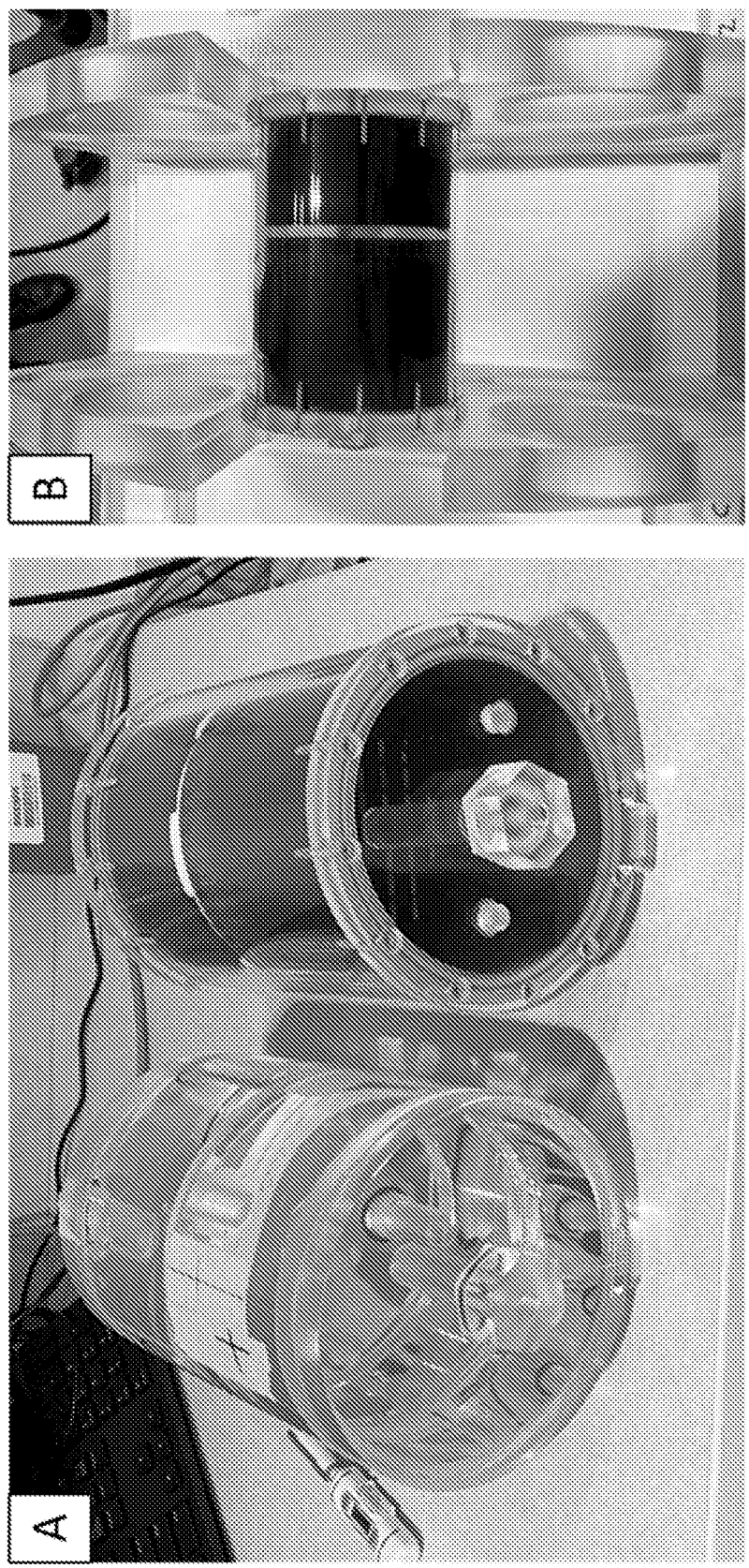
FIG. 2A is a photograph comparing the manufacturer daily QA phantom (left) and an embodiment of the phantom disclosed herein (right)
FIG. 2B is a photograph showing compatibility of the manufacturer provided jig with the phantom.
Figure 3:
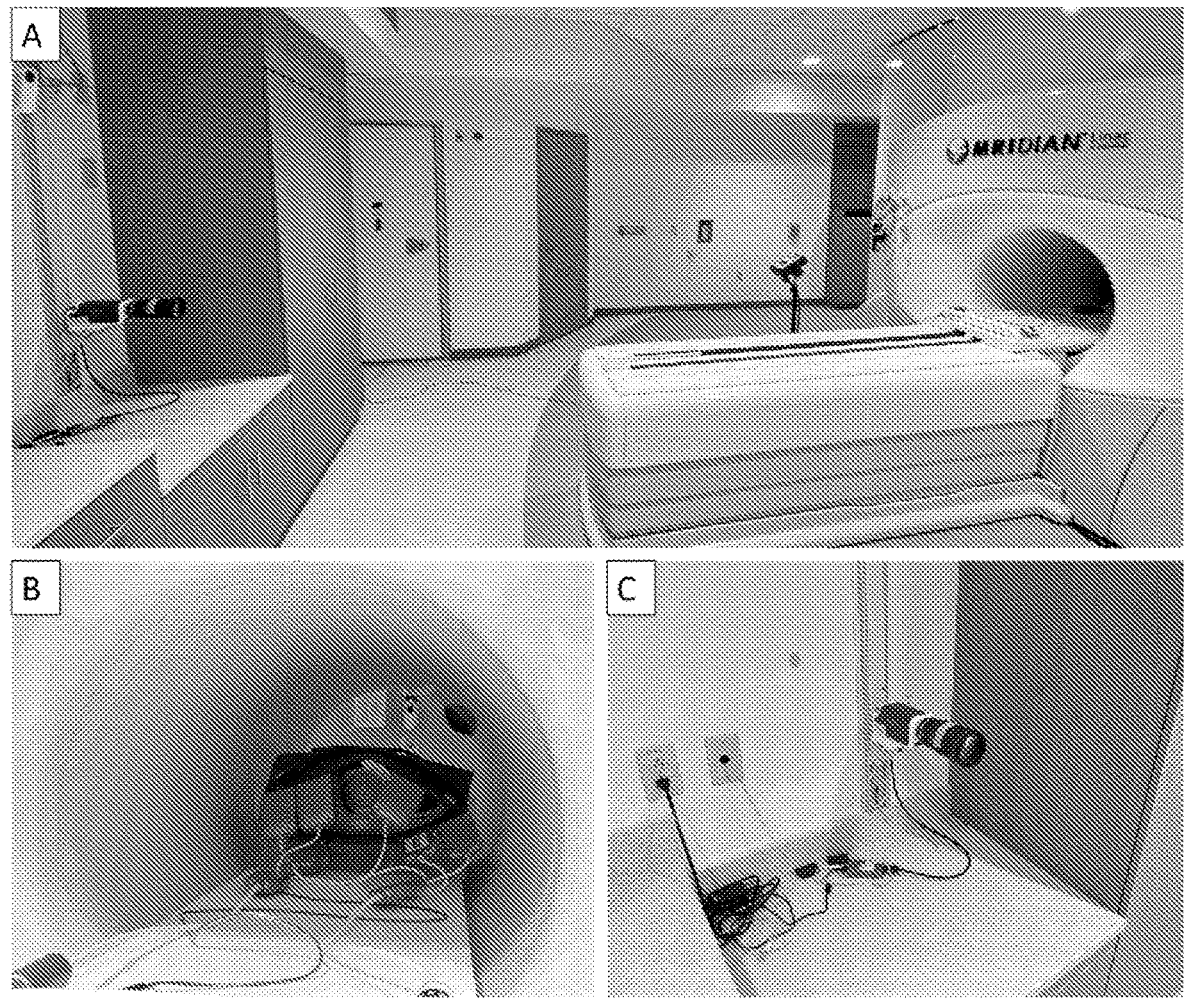
FIG. 3A is a photograph of the treatment bunker with a camera mounted relative to the MR-Linac.
FIG. 3B is a photograph of the phantom aligned with imaging coils in the bore.
FIG. 3C is a photograph of the wall-mounted camera aligned along the longitudinal axis.
Figure 4:
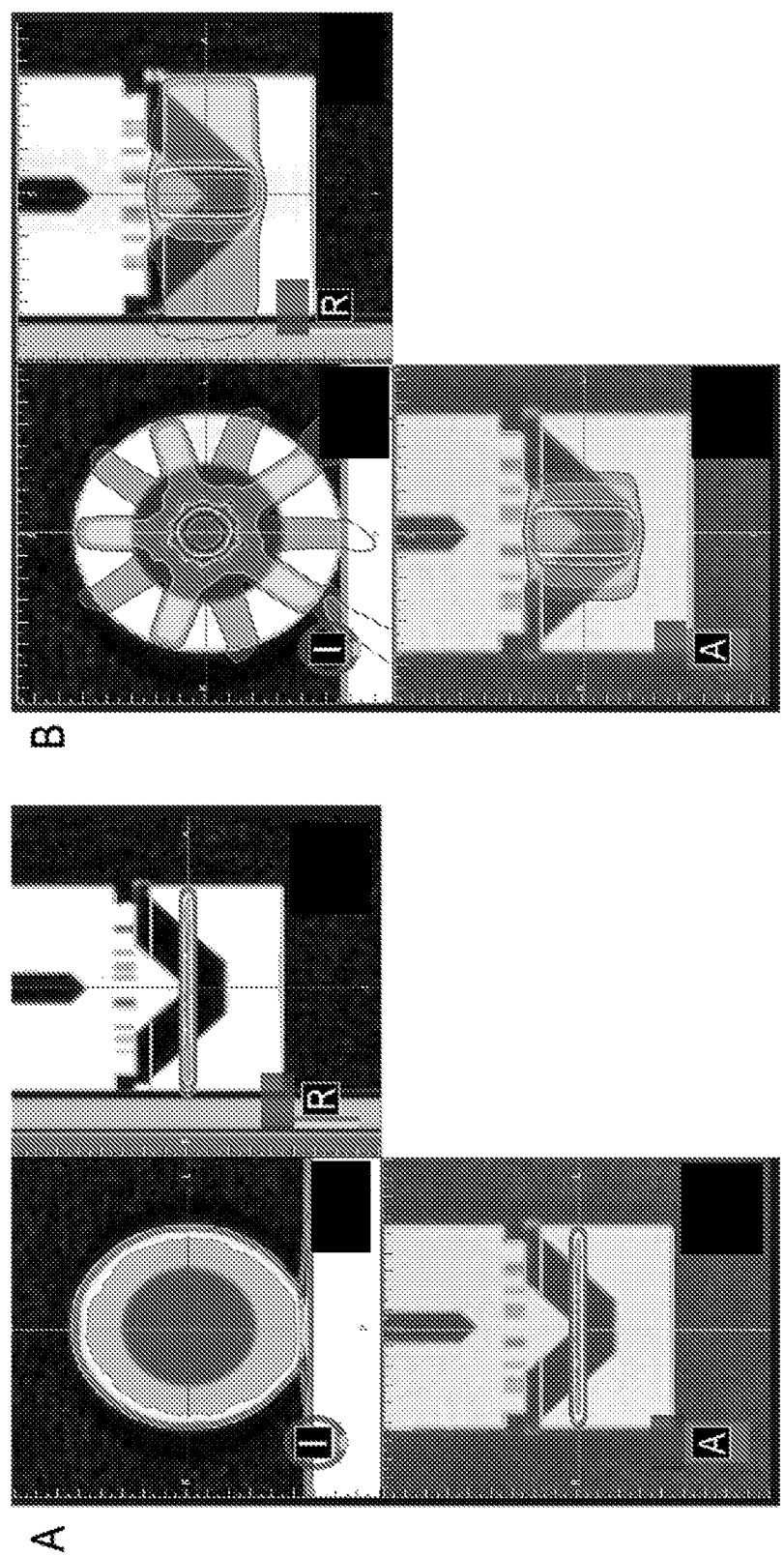
FIG. 4A shows dose distributions overlaid on the MR images of the phantom for the sheet irradiation.
FIG. 4B shows dose distributions overlaid on the MR images of the phantom for the star shot.

The system includes an isocenter coincidence phantom 100, which was designed with added functionality and to be similar in shape and dimensions to the existing MRIdian daily QA phantom such that it included of a cylindrical acrylic body filled with water. FIGS. 1(a)-1(c) show the design of the phantom as rendered from SOLIDWORKS (Dassault Systemes SOLIDWORKS Corp., Waltham MA, USA). The outer housing was composed of four custom-machined pieces of clear acrylic: a front end cap 107, rear end cap 108, cylindrical body 104, and rear hollowed plug 110 for ion chamber insertion. The two circular end caps 107, 108 each with a diameter of 13.85 cm were machined out of 0.5-inch thick sheets of acrylic. The front and rear end caps 107, 108 each had a flattened bottom side with a protruding tab to be compatible with ViewRay daily QA phantom's jig for couch mounting, as shown in FIG. 2A. In an instance, the cylindrical body of the phantom 100 had a smaller outer diameter than the caps at 5.25 inch and an inner diameter of 4.5 inch, with a length of about 6.5 inch. Each end cap 107, 108 was attached to the cylindrical body 104 using 12 countersunk M3 PEEK screws (see FIG. 1C), and a water-tight seal was obtained with a 1/16 inch wide O-ring 105, 106 placed in a machined groove in each end cap 107, 108.

While the outer face of the front end cap 107 was untouched for optical imaging, three holes were threaded through the rear end cap 108. Two symmetric 1/4 NPT holes hosted quick-turn couplings for simplified connection to a water pump for air-bubble removal, while a central threaded port hosted the O-ring sealed hollow plug 110. The hollow plug 110 design contained a hollow port for insertion of an MR-compatible A28 ionization chamber for daily output measurements as shown in FIG. 1B. The ionization chamber is a small radiation dose measurement detector used for standard machine dose measurements in a water tank. This can provide omni-directional spatial resolution for relative dosimetry scanning in water phantoms and use in small field measurements.

As shown in FIG. 1C, the four inner components of the phantom 100 in order from rear to front included a rear spacer 101, radioluminescent conical frustum 102, and front spacer 103. The conical frustum 102 can be fabricated of a light-colored plastic (e.g., white) to provide the radioluminescent function. The inner components can be circular with outer diameters coincident with the inner diameter of the cylindrical body 104 for secure assembly. The two spacers 101, 103 were 3D printed using black filament and were used to hold the central features of the design in place within the cylindrical body 104. Each spacer 101, 103 interfaced with their respective end caps 107 and 108 via two additional O-rings 105 and 106, which were concentric with the couplings between the end caps 107 and 108 and cylindrical body 104 to ensure a tight fit of the internal components. FIG. 1C shows the O-rings as "2×," but this can refer to one between the cylindrical body 104 and the rear end cap 108 and one between the cylindrical body 104 and the front end cap 107. Of course, more than one O-ring can be used adjacent the end caps 107, 108. Matte black filament was used in printing to minimize potential optical reflections and leakage from the transparent outer acrylic. The length of the rear spacer 101 was specified such that it would clear the outer length of the hollow plug 110 for the ion chamber.

In an instance, a grid component 109 can optionally be included with the conical frustum. The grid component 109 can be a 1 cm spaced square grid inscribed in the circular profile of a 1 cm thick disk, was also 3D printed using black matte filament. This optional grid component 109 was included for potential MRI spatial distortion tests and was held between the rear spacer 101 and conical frustum 102.

The conical frustum 102 was the primary component of the phantom 101 design and was milled out of white ABS plastic. Ionizing radiation passing through the plastic yields Cherenkov emission, as does radiation passing through the surrounding water; however, Cherenkov photons in the plastic undergo multiple scattering events, thereby removing most if not all of the original directionality of the emission when compared to the photon distribution in water. This increases the amount of light emitted from the ABS target that makes it to the camera, providing optical contrast between the plastic and water in the Cherenkov image. The slope of the edge of the conical frustum 102 was 45° from the plane of the image to allow for 1:1 encoding of cone diameter to axial position. Other angles for the conical frustum 102 are feasible, such as 30° to 60° from the plane of the image. The front-facing side of the conical frustum 102 was etched with a crosshair during machining, as well as a thin ring around the sloped face, which when combined provide the physical center of the component. Black paint was applied to these features to increase contrast in the optical background images. On the rear side of the conical frustum 102 there was a hollow cone-shaped cavity, the tip of which was coincident with the markings on the front side. When submerged this cavity filled with water, and the tip of the cavity was visible on an MR image due to the high contrast between plastic and water. This increases the amount of light emitted from the ABS target that makes it to the camera, providing optical contrast between the plastic and water in the Cherenkov image.

All measurements were made on the MRIdian MR-Linac system with MRI scanning and the single 6 MV flattening filter free (FFF) X-ray beam. The phantom disclosed herein was placed in the jig and purposefully aligned with offsets of 2 cm from the lasers in each direction and sent to isocenter after the imaging coils were in place, with caution taken to keep the viewport clear from the camera perspective. First, the phantom was scanned with a built-in sequence with the highest spatial resolution available (i.e., 92 s scanning time and a voxel size of 0.15 cm in each dimension). The center point of the conical structure was isolated on the scan, and appropriate shifts were applied to co-align this point with the coordinates (0, 0, 0) on the MR image. After repositioning, a second identical scan was taken and used as the baseline scan for the system. For all subsequent isocenter coincidence measurements, the phantom was always aligned to −2 cm in each direction, and appropriate shifts were obtained from the image registration built in to the ViewRay console, ensuring alignment of the phantom center with the imaging center.

For the measurement of the radiation isocenter, two custom plans were developed, as shown in FIGS. 4A and 4B. The first plan was a star shot (FIG. 4B) consisting of five equally spaced beams at angles of 0, 72, 144, 216, and 288 degrees. Each beam was a 1.5 cm (lateral, X)×5 cm (longitudinal, Y) centered rectangle, and was optimized to deliver 100 cGy per field to the center of the phantom, resulting in a delivery of 684.6 monitor units (MU). The second plan consisted of four wide sheet beams (FIG. 4A) with dimensions of 27.4 cm (lateral, X)×0.83 cm (longitudinal, Y) at the four cardinal angles of 0, 90, 180, and 270 degrees, which when intersected with the conical structure generated a ring of Cherenkov emission. This second field size reflects the maximum and minimum field width in the lateral and longitudinal dimensions, respectively, in order to achieve the broadest and thinnest sheet of radiation possible. This plan was optimized for 150 cGy per field to the phantom center, which resulted in a delivery of 858.3 MU.

Each plan was delivered and imaged using a custom C-Dose camera (DoseOptics LLC, Lebanon, New Hampshire, USA) and the accompanying C-Dose Research software. Cumulative, background-subtracted Cherenkov images as well as cumulative background images were acquired at 17 Hz. Acquired image dimensions were 1920 by 1200 pixels. The software featured real-time background subtraction, which allowed the room lights to remain on and, therefore, features of the phantom to be readily discernable in the background images. The camera was outfitted with a blue-sensitive image intensifier to increase the blue-weighted Cherenkov signal in the phantom. The camera was fixed with a 200 mm lens (Canon Inc., Tokyo, Japan) with an aperture of f/6.8, and mounted to the wall such that the optical axis aligned vertically and laterally with isocenter, at a distance of 5 m longitudinally. The aperture size used provided sufficient depth of field such that the entire conical structure was in focus.

A standalone application written in MATLAB was deployed on a clinical workstation, which was used to analyze the cumulative images acquired (one Cherenkov image and one background image for each plan noted in the previous section). The data can be analyzed on-the-spot by a user without the need for post-processing and analysis. The application design included four tabs for the different portions of the analysis: isocenter coincidence in the x-z plane, isocenter coincidence along the y-axis, three-dimensional results, and calibration.

The first portion of the analysis software was designed to perform a star shot analysis on the first set of images to assess the radiotherapy isocenter coincidence in the lateral (x) and vertical (z) directions. First, both the Cherenkov and background images can be loaded into the application, and a flat-field correction can be applied to both images. Next, the center of the crosshair can be selected the background by the user, and the software can automatically detect the true center by assessing a 10 mm radial profile around the point clicked and finding the intersection point of the two lines. This resulting point is taken as the phantom center in the x-z plane.

Next, the user can specify the number of beams used in the star shot and can manipulate a circular ROI on the Cherenkov image around the edge of the star shot pattern. The radial profile used to find the peaks of each beam may be an average of ten concentric profiles centered around the user-drawn circle that is then median-filtered with a 5-pixel moving window. Then, the resulting radial profile can be rescaled from −1 to 1, and all zero crossings are determined. The peaks can be taken as the midpoints of these zero crossings corresponding to positive values on the profile, and the number of peaks can be cross-checked with the user-defined value. Opposing peaks can then be joined by line segments. The median of the $(n^2-n)/2$ intersection points of these segments may be taken as the start for a search for the minimum circle. After the minimum circle is found, the center point of that circle may be taken as the position of the radiation isocenter in the x-z plane.

The second portion of the analysis software was designed to measure the physical longitudinal distance between the phantom center and radiation field center. First, both the Cherenkov and background images of the second treatment plan can be loaded into the software in an identical manner as that described above. Next, using a circular ROI-drawing tool, the etched ring can be outlined by the user on the background image. A short 5 mm radial profile can then be acquired at and centered on each point along the outline of drawn ROI. The position of minimum pixel value along each profile can be taken to be the position of the ring outline at that angle. These values can then be averaged across all angles to determine the radius of the ring in the background image.

Next, the average radius of the optical ring displayed in the Cherenkov image can be calculated automatically by software in three steps. First, a radial profile starting from the center point (as defined by the crosshair position determined prior) is acquired at each angle. Second, the average position of the 40% maximum values along the rising and falling edge of each profile is taken to be the radius of the optical ring at the corresponding angle. Third, the average radius over all angles is calculated and displayed.

Lastly, the diameters of the etched ring in the background image and the optical ring in the Cherenkov image can be subtracted, and the resulting difference can be mapped to a longitudinal difference in the y-positions of the phantom center and the radiation isocenter via a linear fit determined from a pre-defined calibration curve.

After the first and second portions of the analysis are complete, the differences between the phantom center and radiation isocenter in each of the three dimensions, dx, dy, and dz, can be displayed along with the 3D vector magnitude dr. For each of these quantities, the numerical value can be displayed in one color if the absolute value falls below the TG-142 threshold of 2 mm in an example. In this example, it otherwise can be displayed in another color. TG-142 is the Task Group Report No. 142 from the American Association of Physicists in Medicine, titled "Quality assurance of medical accelerators." This standard provides guidance on routine quality assurance procedures performed by medical physicists.

The software can use three calibration steps in order to perform flat-field image import, pixel size definition, and diameter-to-longitudinal position calibration. Flat-field images are performed with the camera in an identical physical configuration to the normal operating state and can be acquired with the C-Dose Research software using, for example, flood illumination via an 8 inch×8 inch uniform LED board (Advanced Illumination, Rochester, Vermont, USA). The frame-averaged image can then be loaded into the software and normalized, and subsequently all loaded Cherenkov and background images can be divided by this flat-field image to correct for vignetting and intensifier artifacts. The pixel size is determined by measuring a known feature on the phantom, such as the crosshair width on the conical structure in the phantom. This value can then be used for pixel to mm conversion in all analysis steps.

The diameter to-longitudinal position calibration can be performed by imaging the phantom under a specific set of pre-determined conditions. First, the phantom is aligned to the center of the MR image, in an identical fashion to daily setup prior to irradiation. Next, the plan containing the four sheet beams of radiation is delivered while Cherenkov images are being acquired. This is repeated five more times at longitudinal shifts (in mm) of −5, −2.5, −1, 1, and 2.5. At each longitudinal position, the radii of the physical and optical rings are calculated on the cumulative Cherenkov and background images, respectively, using the methods described herein. A linear fit can be performed between the differences in the two diameters at each position and the corresponding longitudinal shifts. The fit parameters can be saved and are subsequently applied to the measured differences in the ring radii during analysis.

To test the validity of the novel methods described, two comparative measurements were made in an example. First, the Cherenkov star shot image was analyzed using the open-source Python library Pylinac to assess both the calculated minimum circle radius and the x-z radiation isocenter position thereby validating the efficacy of the x-z analysis protocol. Second, the 3D isocenter was measured using the vendor-recommended film-based method described above and with vendor-provided analysis software to verify agreement between the accepted method and embodiments disclosed herein.

Using the pixel measurement of the known diameter of the front face of the conical structure (28 mm), the physical size in the imaging plane represented by one pixel was determined to be 0.24 mm. FIG. 5 shows select Cherenkov images and radial profiles resulting from the diameter-to-longitudinal position calibration described previously. The diameter of the etched ring in the corresponding background images of the phantom was found to be 63 mm, matching the dimension measured in SOLIDWORKS. This value was subtracted from each of the measured optical ring diameters (radii marked with vertical lines on the radial position in FIG. 5) and plotted against the known longitudinal shifts. The resulting plot and linear fit are also shown. These numerical data are displayed in Table 1.

TABLE 1

Correspondence between observed optical diameter shift sand linear axial shifts.

| Optical Diameter Shift (mm) | Linear axial shift (mm) |
|---|---|
| 7.93 | −5.0 |
| 3.12 | −2.5 |
| 0.21 | −1.0 |
| −1.97 | 0.0 |
| −4.23 | 1.0 |
| −7.08 | 2.5 |

The relationship between the shift and optical ring diameter was found to be linear with an $R^2$ value of 0.997. Additionally, the root-mean-square error was calculated as 0.184 mm, which gives an idea of the uncertainty in the y-position measurement. The extracted fit coefficients were used subsequently in the longitudinal isocenter coincidence analysis.

FIGS. 6A-6D show both the lateral-vertical and longitudinal components of the analysis, captured from the custom application. FIG. 6A shows the background image of the phantom, including the view of the crosshair. FIG. 6B shows the Cherenkov image used in the longitudinal analysis, which utilizes the calibration curve calculated previously in FIG. 5. The physical diameter of the etched ring was found to be 63.34 mm, and the optical diameter was found to be 62.33 mm, yielding a diameter difference of 1.01 mm. The star shot image is shown in FIG. 6C, and the corresponding radial profile along with the beam peaks is displayed with a remapped x-axis to match the coordinate system used by ViewRay in FIG. 6D; using this data, the radius of the minimum circle was found to be 0.34 mm.

Based on the image analysis, the following differences between the phantom center and radiation isocenter were calculated: dx=−0.61 mm, dy=0.55 mm, dz=−0.14 mm, dr=0.83 mm. These results show that the isocenter coincidence is within the 2 mm tolerance described in TG-142.

The output from the Pylinac star shot analysis module reported a minimum circle radius of 3.75 mm and an x-z radiation isocenter position relative to the software result of Δx=0.29 mm and Δz=0.94 mm (1.1 and 3.9 pixels respectively). The results of the 3D MR-RT isocenter coincidence from the vendor-recommended film-based method were found to be $dx_{Film}$=−0.31 mm, $dy_{Film}$=0.15 mm, $dz_{Film}$=0.79 mm, and $dr_{Film}$=0.86 mm.

Based on these results, the system represents a near-real-time alternative to currently used film-based solutions for imaging-radiation isocenter coincidence verification. This makes embodiments disclosed herein a feasible method for measuring this parameter on a daily basis. Additionally, the software developed as part of this system can be used by all clinical personnel immediately after data acquisition. The inclusion of an ionization chamber housing allows this phantom to be used for output measurements as well, with comparison to baseline of either an off-axis field irradiation, an off-axis chamber measurement, or a known longitudinal couch shift to center the chamber. This combination of developments allows this phantom to perform all TG-142 dosimetric measurements for MR-Linac daily QA. Additionally, the analysis results, in 3D and along each axis, were found to be within 1 mm agreement both with the output from the Pylinac star shot analysis of the Cherenkov image as well as the film-based method results.

The analysis procedure including the use of the software application designed for this system may require the consistency of three calibration settings: the flat field image, the pixel size, and the diameter-to-longitudinal position calibration. The flat field image may be important to correct for relative intensity differences in different regions of the image due to vignetting and intensifier defects, and this feature remains unchanged in the absence of physical camera modifications, such as internal adjustments or lens replacement. The pixel size can be sensitive to changes in the imaging plane, such as focus and camera position, and may be cross-checked on a regular basis to ensure there are no physical changes to the system. However, the aperture can be set small to ensure that the depth of focus is large enough to keep the entire depth of the conical structure in focus. In an instance, the 200 mm lens was chosen to optimize the resolution and field of view, as the camera is mounted 5 m from the isocenter (out of the 5 gauss line), but also to achieve an image closer to a true orthographic projection of the phantom to avoid analysis considerations from the perspective view. The diameter-to-longitudinal position calibration can be crucial to the efficacy of the y-axis analysis and is similarly sensitive to camera position and focus as the pixel size. However, this is mitigated by the camera mount, which may only allow for rotational adjustment in the lateral and vertical directions and can be tightly fixed after initial setup. Still, the image field of view may be checked for positional changes on a routine basis to ensure continued viability of the calibration.

One effect that was observed was the systematic offset in apparent optical diameter compared to the physical diameter of the intersection ring as a given longitudinal position. As shown in FIG. 5 and Table 1, there is a −2 mm offset in the apparent diameter. This is explained by the fact that Cherenkov light produced deeper in the ABS conical structure compared to the surface is able to diffuse upward along the inner outline of the ring, which can bias the diameter measurement downward. This effect can be corrected for in the linear calibration step, however. Additionally, in the optical diameter calculation, the decision to use specifically 40% of the maximum intensity as the rising and falling edges on the averaged radial profile, as opposed to 50% for example, was made in order to avoid the subtractive impact of the etched ring on the absolute intensity value. This compromise yielded the most consistent replication of the true location of the radiation isocenter.

While the camera and DC power supply were kept out of the 5 gauss line, there was a small effect on MR image quality when the power supply was plugged into the wall outlet, likely due to interfering radiofrequency noise. This is likely related to powering the camera, as data is transmitted from the camera to the console over fiber, though other mechanisms are possible. To avoid any possible distortions, the camera may be powered only when irradiating the phantom and unplugged during MR imaging.

The use of a 2 mm tolerance for the isocenter coincidence measurement is based off the TG-142 Report guidelines for non-SRS/SBRT treatments, however there is no such guideline specifically for MR-guided external beam radiotherapy treatments. With the prevalence of daily adaptive planning for such treatments using newly acquired imaging, as well as the common use of hypofractionation, it may be difficult to determine what the correct tolerance should be for this application. The 2 mm tolerance was applied for agreement with prior studies and other values may be possible.

The spatial resolution of the available scan sequences may be limited to 1.5 mm×1.5 mm×1.5 mm. While this is not necessarily the granularity of the image registration algorithm providing the couch shifts, it is a factor that can limit measurement resolution. This positioning uncertainty has been estimated previously at 0.5 mm. This could explain some of the discrepancy between the measurements made by the system and those made using other programs and methods.

A longitudinal assessment of this method can be compared to both film and ion chamber profiler-based isocenter coincidence verification methods, as well as tracking dose and dose rate constancy using an embedded ion chamber in the phantom compared with the manufacturer-provided daily QA phantom. Additionally, development of a time-gated, non-intensified camera may reduce the cost of implementing a system such as this in the clinic, though a typical off-the-shelf camera with sufficient exposure settings also may work in this application. Lastly, although designed for MR-Linac QA, embodiments disclosed herein can be applied to conventional accelerators with kV imaging.

Summarizing this example, a fully enclosed and sealed acrylic cylindrical phantom was designed to be mountable to the manufacturer-provided jig. A custom-machined plastic conical structure was fixed inside the phantom and held in place with 3D-printed spacers. The phantom was filled with water, allowing for high edge contrast of the plastic cone on MR images. Both a star shot plan and a four-angle sheet beam plan were developed and delivered to the phantom. The former allowed for radiation isocenter localization in the x-z plane (A/P and L/R directions) relative to physical landmarks on the phantom. The latter allowed for the longitudinal position of the sheet beam to be encoded as a ring of Cherenkov radiation emitted from the phantom, allowing for isocenter localization on the y-axis (S/I directions). The disclosed software application was performed near-real-time analysis of the data.

Calibration procedures showed that linearity between longitudinal position and optical ring diameter is high ($R^2>0.99$), and that RMSE is low (0.184 mm). The star shot analysis showed a minimum circle radius of 0.34 mm. The final isocenter coincidence measurements in the lateral, longitudinal, and vertical directions were −0.61 mm, 0.55 mm, and −0.14 mm respectively, and the resulting 3D coincidence was 0.83 mm, below the 2 mm tolerance defined in TG-142. Longitudinal analysis showed an average coincidence of 1.5 mm 0.4 mm over eight weeks of daily use.

These results demonstrate an efficient method for acquisition and near-real-time analysis of MR-Linac isocenter coincidence data and represents a direct measurement of the 3D isocentricity. This phantom and analysis application combined with longitudinal analysis makes this solution an option for clinical use.

The disclosed herein can provide convenient, streamlined, and near-real-time measurement of imaging-radiation isocenter coincidence verification for MR-Linac systems, overcoming the disadvantages of traditional film-based methods. The fully enclosed phantom design and analysis software yield a robust solution for MR-Linac daily QA.

The disclosed examples are merely possible implementations. These examples are not meant to be limiting.

The method disclosed herein can use a personal computer system, image computer, mainframe computer system, workstation, network appliance, internet appliance, or other device. The sub-system(s) or system(s) may also include any suitable processor known in the art, such as a parallel processor. In addition, the sub-system(s) or system(s) may include a platform with high speed processing and software, either as a standalone or a networked tool.

In some embodiments, various steps, functions, and/or operations disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape, and the like. A carrier medium may include a transmission medium such as a wire, cable, or wireless transmission link. For instance, the various steps described throughout the present disclosure may be carried out by a single processor (or computer system) or, alternatively, multiple process (or multiple computer systems). Moreover, different sub-systems may include one or more computing or logic systems. Therefore, the above description should not be interpreted as a limitation on the present disclosure but merely an illustration.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof

What is claimed is:

1. A system comprising:
   a cylindrical phantom; and
   a conical structure disposed in the phantom, wherein the conical structure is shaped as a frustum and wherein the conical structure emits Cherenkov radiation when exposed to ionizing radiation.

2. The system of claim 1, wherein the conical structure is a radioluminescent material configured to enhance signal-to-noise.

3. The system of claim 1, wherein the conical structure is fully enclosed in the cylindrical phantom.

4. The system of claim 1, wherein the conical structure is held using spacers.

5. The system of claim 1, wherein the cylindrical phantom is sealed thereby being capable of holding a liquid.

6. The system of claim 1, wherein an outer housing of the cylindrical phantom defines a hollowed plug configured to hold an ion chamber.

7. The system of claim 6, wherein the conical structure further includes a crosshair and a ring on a surface opposite the hollowed plug whereby the crosshair and the ring are used for lateral, vertical, and axial alignment.

8. The system of claim 1, wherein the conical structure defines a cavity in the interior of the frustum that comes to a point at a center of the cylindrical phantom.

9. A method comprising:
   providing a system that includes a cylindrical phantom and a conical structure disposed in the phantom, wherein the conical structure is shaped as a frustum and wherein the conical structure emits Cherenkov radiation when exposed to ionizing radiation; and
   exposing the system to ionizing radiation; and
   calibrating, using a processor, an MR-Linac using measurements from the exposing.

10. The method of claim 9, wherein the Cherenkov radiation is imaged during exposure to ionizing radiation.

11. The method of claim 9, wherein the cylindrical phantom is configured to be a surrogate of radiation dose to the conical structure such that distribution of the radiation dose delivered to the system in the imaging plane is determined.

12. The method of claim 9, wherein the cylindrical phantom is irradiated with a sheet of radiation parallel to an imaging plane and that is smaller than a height of the conical structure thereby providing a diameter of a circular intersection of the radiation with the conical structure and providing an axial position of the radiation.

13. The method of claim 9, wherein the calibration includes measurement in three dimensions of an isocenter of the system relative to a position of the cylindrical phantom using marks on a surface of the conical structure.

14. The method of claim 9, wherein the calibration uses a flat field image, a pixel size, and/or a diameter-to-longitudinal position calibration.

15. The method of claim 9, wherein a Cherenkov image and/or a star shot image is used to determine a difference between a center of the cylindrical phantom and a radiation isocenter.

16. The method of claim 9, wherein the processor is in electronic communication with a camera.

17. A computer program product comprising a non-transitory computer readable storage medium having a computer readable program embodied therewith, the computer readable program configured to carry out the calibrating of claim 9.

* * * * *